(12) United States Patent
Gandarias (10) Patent No.: US 6,843,769 B1
(45) Date of Patent: Jan. 18, 2005

(54) OPTICAL LUMINOUS LARYNGOSCOPE (75) Inventor: Pedro Acha Gandarias, Vizcaya Getxo (ES)

(73) Assignee: Page 65, S.L. (ES)

( * ) Notice: Subject to any disclaimer, the term of this patent is extended or adjusted under 35 U.S.C. 154(b) by 0 days.

(21) Appl. No.: 10/257,918

(22) PCT Filed: Oct. 4, 2000

(86) PCT No.: PCT/ES00/00376
§ 371 (c)(1),
(2), (4) Date: Feb. 20, 2003

(87) PCT Pub. No.: WO01/78582
PCT Pub. Date: Oct. 25, 2001

(30) Foreign Application Priority Data

Apr. 18, 2000 (ES) .......................... 200001004
Apr. 18, 2000 (ES) .......................... 200001005

(51) Int. Cl.[7] .............................................. A61B 1/267
(52) U.S. Cl. ....................... 600/189; 600/185; 600/188; 600/190
(58) Field of Search ................................ 600/184, 185, 600/188, 189, 190, 191, 201, 210, 245, 246, 194

(56) References Cited

U.S. PATENT DOCUMENTS 3,513,835 A * 5/1970 Ceuster ..................... 600/218
3,643,654 A 2/1972 Felbarg
4,086,919 A * 5/1978 Bullard ....................... 600/188
4,611,579 A 9/1986 Bellhouse
5,645,519 A * 7/1997 Lee et al. ................... 600/114
6,004,263 A 12/1999 Nakaichi et al.

FOREIGN PATENT DOCUMENTS

| | | |
|---|---|---|
| EP | 0030014 | 6/1981 |
| ES | 1037366 | 2/1998 |
| WO | WO 99/47038 | 9/1999 |

* cited by examiner

Primary Examiner—Beverly M. Flanagan
(74) Attorney, Agent, or Firm—Nixon Peabody LLP; Jeffrey L. Costellia (57) ABSTRACT This invention refers to an optical-light emitting laryngoscope, consisting of a body (1) that contains two independent ducts (3, 4), one of which is free while the other contains optical elements (12), with a straight section followed by a section that is anatomically curved, the end of which is finished by three guide walls (16) for the oral-tracheal tube that has been inserted, while it is possible to observe the movements of the same in a real image through a magnification lens (6) and the optical elements (12), the optical duct being protected by a transparent shell (30), achieving correct positioning of the oral-tracheal tube (15), this invention being designed for oral-tracheal intubation, in operating theaters, emergency wards and out-patient facilities, etc. The body of the laryngoscope (31) may contain a single duct (4) which contains the optical elements (12).

30 Claims, 9 Drawing Sheets

OPTICAL LUMINOUS LARYNGOSCOPE

THE SUBJECT OF THE INVENTION

The optical-light emitting laryngoscope which is the subject of this invention consists of a medical device equipped with optical means of visualising the inside of the trachea, for use in oral-tracheal or nasotracheal intubation, in operating theatres, emergency wards, out-patient and other similar facilities. Likewise, this invention may be used in all types of circumstances in which oral-tracheal or nasotracheal intubation is necessary, due to its simplicity and efficacy.

DESCRIPTION OF THE STATE OF THE ART

In the current State of the Art several different systems are used for oral-tracheal or nasotracheal intubation, in which different tools are used to hold the tongue within the body, thereby clearing the respiratory tract and making it possible to insert a suitable tube for gaining access to the trachea and thus making mechanical respiration possible.

There are several alternative techniques that can be divided into two main categories, of surgical and non-surgical methods, of which the former are avoided whenever possible. It is because of this that the tendency is to perfect non-surgical methods, and a range of items and techniques are currently used to make oral-tracheal or nasotracheal intubation possible.

Due to the anatomical location, close to the point of the opening of the trachea with the epiglottis and the inlet of the oesophagus, the introduction of a tube that makes it possible to use a respirator on a patient is complicated by the fact that the said entry point is hard to see, giving rise to a high risk of introducing the endotracheal tube into the oesophagus instead of the trachea, with the risk of the patient dying if the tube is not extracted from the oesophagus and inserted into the trachea.

The means that are currently used to isolate the airway of a patient give rise to different risks, which increase the possibility of death for the same. These intubation devices are usually employed in extreme situations, i.e., in cases in which time is a highly important factor, which complicates the intubation process considerably, although they are also used in operating theatres for programmed operations, apparently without risk.

As was pointed out above, different guides or laryngoscopes are used for intubating human patients. The ones most widely used are described below, as well as others which are known but in disuse because of the danger of using them.

The most widely used laryngoscopes are of the blade type, and are composed of a handle and a blade or guide that is perpendicular to the same. This is the case for American patent U.S. Pat. No. 5,003,962, in which a blade with three straight sections at angles to each other may be observed. Nevertheless, this does not resolve the chief problem with blades, which consists of blind intubation, without being able to see the opening of the trachea, and they also require the neck to be bent in an exaggerated manner. American patent U.S. Pat. No. 5,349,943 describes another bladed laryngoscope, by Ruiz, and in this case the neck is not required to turn so far, as one of the ends of this laryngoscope holds a mirror. This mirror allows the user of the laryngoscope, usually a doctor, to see an inverted image that impedes the introduction of the endotracheal tube. In spite of its being an improvement on the previous laryngoscope, blind intubation is still necessary.

There are also laryngoscopes that incorporate optic fibre to avoid intubation taking place blind, although the use of optic fibre makes the product excessively expensive. One laryngoscope that includes optic fibre is the one described in patent application EP0030014, by Upsher. The main problem with optic fibre is the price of the same, as it means that laryngoscopes have to be reused to justify their cost. These optic fibre laryngoscopes therefore have to be subjected to processes of disinfection and sterilisation, either in an autoclave or by chemical processes, which give rise to the loss of the characteristics and quality of the optic fibre, while the complete disinfection of the laryngoscope is never fully guaranteed, with the consequent danger of transmitting diseases and viruses from one patient to another.

There are other methods of intubation which do not oblige patients to turn their necks in excess, and this is the case with European patent application EP0284335, by Augustine, which describes a laryngoscope that makes it possible to insert a tube without the neck being turned. Nevertheless, the patient has to be lying down, and moreover intubation takes place blind.

Another type of device for intubation is described in American patents U.S. Pat. No. 5,665,052 and U.S. Pat. No. 4,905,669, by Bullard, and U.S. Pat. No. 5,095,888, by Hawley. These describe laryngoscopes that are used for the correct introduction of the oral-tracheal tube in the trachea by means of a stylet or wire combined with optic fibre. The said stylet is inserted into the oral-tracheal tube and is then joined onto the main body of the laryngoscope, after which the whole set is placed inside the patient. The main problem with this method is that the point of the stylet always protrudes from the end of the tube when it is inserted, due to its lack of stability, and therefore wounds the larynx or the opening of the trachea due to its movement. Due to the deviation of the point of the stylet, in the same way as the ones described above this device does not ensure the correct introduction of the endotracheal tube into the trachea of the patient.

The devices that are usually used in intubations consist of guides or blades, as briefly described above, which are used to make it possible to see the opening of the trachea before then proceeding to insert the endotracheal tube. A range of problems arising from the use of this type of widely employed laryngoscope are described below.

Due to the shape of these blades patients are forced to assume a highly uncomfortable position in order to make it possible to observe the tracheal zone. The patient always has to be in a horizontal position, with the neck bent backwards as far as possible, this being necessary to make it possible to see the opening of the trachea. Excessive extension of the cervical area in this position, in case of accidents, patients with multiple trauma or individuals with cervical problems may be hazardous. Moreover, the obligation to place the patient in the said position makes it impossible to intubate accident victims who are trapped and unable to move.

Once the patient has been placed in the position described above the blade is inserted, there being different types and configurations of these for the usual visualization of the opening of the trachea. Once this point has been discovered and when the orifice is visible the endotracheal tube is inserted, and this leads to the opening of the trachea ceasing to be visible, so that the tube has to be inserted blind. Due to this, tracheal intubation is highly complicated, as it is impossible to know at any time if the tube has been inserted into the trachea or oesophagus. Moreover control is lost of the position of the tube during the operation.

The process of intubation is slowed down because of the above problem, and this places patients' lives in danger, as this process has to take place as quickly as possible to allow the individual to breathe.

Depending on the characteristics of the patient, the use of oral-tracheal blades or guides may require so much force to insert them, as well as to be able to observe the point of entry of the breathing tube into the trachea, that wounds are caused to the inside of the mouth, and teeth may even be broken. The sex, height and degree of obesity of patients also influence the degree of difficulty, as well as the duration of the intubation process.

It is possible that during the introduction of the blade, items or foreign bodies which are dangerous for the patient may be observed in the airway, but due to the impossibility of inserting elements while observing the inside of the duct at the same time it is impossible to extract the said bodies, because of the difficulty of finding them without sight.

DESCRIPTION OF THE INVENTION

This invention, which covers an optical-light emitting laryngoscope, attains the practical elimination of the problems described above, ensuring that risk is minimum in comparison with traditional methods of oral-tracheal and nasotracheal intubation.

The optical-light emitting laryngoscope described in this invention makes available a device that is optimum for isolating and visualising the airway of a patient, either in an operating theatre for a normal operation, or in emergency situations such as accidents that require an emergency service prior to hospitalisation, taking into account the fact that obstruction of the airway is the most frequent cause of avoidable deaths in unconscious and wounded patients.

In a situation in which the patient is an individual with multiple trauma a method has to be chosen to isolate the airway of the same. This decision, which has to be taken without diagnosing the patient, may be a delicate one, not only because of the severity of the trauma, but also because the time that passes from the moment the event causing the trauma occurred to the moment that the patient arrives at hospital for definitive treatment is decisive for his evolution. It is during this time that pre-hospitalisation emergency services intervene.

When reviving unconscious patients, a priority concern is to attain an airway that is open and stable, while always taking into account the fact that any intervention on the airway of such a patient must take place on the basis of assuming that there may be a cervical injury, so that any unsuitable manipulation could cause greater harm. Although it would be ideal to act on an airway following careful physical examination and radiological checking of the neck, pre-hospital and emergency services do not even have the equipment that would be needed for this, and nor is there time to perform them on many occasions, as the clinical condition of the patient makes it impossible to delay the start of revival manoeuvres, and action is taken directly with the means available at the time.

The optical-light emitting laryngoscope described by this invention is partially inserted in the mouth of the patient, and is composed of a main body as a frame, in which there are two channels or ducts. One end of the laryngoscope remains outside the mouth of the patient, while the opposite end, which is equipped with a light source, is placed within the patient. The light source may be powered from a battery compartment located at the outer end of the laryngoscope, or by another lighting system joined to the main body. Although the main body may vary in cross-section, its components will remain the same. The said body has two different sections: an initial straight section, and a second section that is curved anatomically and which is adaptable to the inside of patients' mouths.

The inside of the main body is divided into two ducts by means of a wall containing the means of transmitting power to the light source. One of the ducts (the visualisation duct) is equipped with the optical means of observing the inside of the larynx. The other duct is empty, and may therefore be used for introducing any instrument or element that is necessary.

The said free duct will be used as a guide, and its end or outlet is equipped with guide walls for the instrument to be inserted, usually a breathing tube for the patient (an oral-tracheal tube). The said angled walls guide the tube towards the target point, which is at the same time being observed through the visualisation duct. This point will usually be the opening of the trachea, to ensure the correct introduction of the oral-tracheal tube. The said guide walls are formed of two centring side walls and a lower wall which raises the oral-tracheal tube or the instrument inserted.

The visualisation duct contains certain optical items that are necessary for the transmission of the image from the end of the laryngoscope that is within the patient to the opposite end, outside, where there is a magnification lens that makes it possible to observe the target point in greater clarity and larger scale. The optical elements are surfaces that reflect the image, and may be mirrors made of glass or plastic. These may be substituted by optic fibre, although they are recommendable as they are cheaper than the second option. The laryngoscope has two optical elements located one after the other in the sector of the anatomical curve, in such a way that they pass the angle of curvature of the duct, and are angled correctly for a target point set beforehand. The reason why two optical or reflecting elements are used is that one reflects the image of the other, thereby giving a real and not inverted image of the target point. The second optical element, or the one that is located close to the tip of the outlet or interior of the laryngoscope, may be slightly angled in relation with the axis of the duct, with the aim of directing vision towards the target point of visualisation. The end of this visualisation duct will be covered by a transparent shell which prevents the entry of foreign bodies.

The said visualisation duct may be configured in different ways by means of small modifications to its components. With the aim of facilitating and cheapening the assembly of the laryngoscopes, and on condition that doing so is more beneficial, it is possible to replace the angled optic element with one that is not angled, on condition that the protective transparent shell is replaced with a prism that directs vision to the target point, or a wide angled lens focused on the said point.

To perform intubation, simply insert the laryngoscope which is the subject of this invention into the mouth of the patient, through the pharynx to the larynx, and once inside, the endotracheal tube is inserted through the guide duct. In those cases in which patients have delicate mouths, as may be the case for the elderly or children, it is possible to insert a laryngoscope equipped with articulated means that make it easier to insert the same in the oral cavity. This articulates to adapt to the patient's mouth, most especially at the location of the curve.

To check whether the tube has been correctly inserted, i.e., that it is inside the trachea and not the oesophagus, the trachea is observed during the introduction process, from the moment when the endotracheal tube is inserted into the guide duct until the end of the said tube appears in our field of vision, when we will see it entering the trachea with the aid of the guide walls at the end of the guide duct. This continuous visualisation allows us to check the length of endotracheal tube that has been inserted, preventing any excessive introduction of the said tube, as this would lead to the dangerous bronchial intubation of a single lung. Additionally the outside of the frame shows a visible measure of the length of the optical-light emitting laryngoscope which will be of aid in checking the length of tube inserted.

The trachea is protected by the epiglottis, which at the moment of swallowing covers the trachea to prevent the entry of food into the respiratory apparatus. To permit access to the trachea this said cartilage will be displaced together with the tongue by the laryngoscope when this is inserted, as the latter is equipped with a blade that may be fixed, or mobile and controllable from the outside.

Once the laryngoscope has been correctly positioned and the patient has been intubed, the former is fixed in place by means of bands affixed to the main body of the laryngoscope that go round the patient's head.

The laryngoscope may be equipped with a bag around its end, connected to the exterior by a tube that makes it possible to inflate the said bag, thereby displacing the walls of the larynx to increase the cavity so that visualisation of the area of the larynx may be improved. In the case of the laryngoscope being used by non-medical health care personnel who are not qualified to insert an endotracheal tube, this may be used as a means of introducing oxygen, using an adapter located in the guide duct for connection to an external oxygen source.

A variation of the configuration described above consists of using a body with a single duct, this being equipped with identical optical equipment to those described above for the visualisation of a target point inside. If the main body only has one duct, it is a simplified optical-light emitting laryngoscope. This laryngoscope is smaller than the one described above, and may be used to locate foreign bodies, as well as for nasotracheal intubation. Usage of this laryngoscope would be restricted to visualising the inside of the mouth, pharynx, larynx and trachea, as well the extraction of foreign bodies by means of introducing suitable instruments via nasotracheal or oral-tracheal. This laryngoscope also makes it possible to perform nasotracheal as well as oral-tracheal intubation, by means of inserting a tube through a patient's nose. The said tube goes through the nasal cavity that joins the nose and mouth. From then on it is necessary to insert the tube with care, until the end of the tube is observed by the laryngoscope, after which it has to be guided to the opening of the trachea.

Clear advantages may be deduced from these configurations in comparison with the methods and laryngoscopes in current use. The said advantages, which are shared by the optical-light emitting laryngoscope with an oral-tracheal guide and the simplified optical-light emitting laryngoscope, given that both cases offer an optimum device that makes it possible to maintain the airway open in a stable manner, with effective ventilation while avoiding violent manipulation of the cervical region, are:

It is possible to use visualisation during the insertion of the tube in the trachea, with safety and precision.

Intubation of the oesophagus is prevented, thanks to continuous visualisation of the manoeuvres performed.

Visual checking is possible throughout the entire medical intervention, while allowing observation at any time of whether the respiratory tube remains in the correct position.

Thanks to its curved anatomical design and continuous visualisation of the inside of the patient, it is unnecessary to force the head and neck of the patient to insert the device, as in the case of accidents, multiple trauma or patients with cervical problems any brusque manipulation of the area of the neck may be dangerous.

It is fast to use, and it is easy to learn how to handle it. This makes it safe to use, ensuring the success of any intervention when the optical-light emitting laryngoscope is employed.

It has a suitable anatomical shape, and adapts to the inside of the mouth up to the larynx.

It may be used in the diagnosis of tumours, to locate internal bleeding or foreign bodies, to insert probes for the suction of blood, fluids or vomit, and the guide duct may also be used to insert different instruments for taking biopsies or inserting bronchoscopes, etc.

It makes it possible to correctly control the manoeuvre of extracting the endotracheal tube, as well as the laryngoscope itself, so as not to leave remnants of any type, such as liquids, clots or foreign bodies which could subsequently obstruct the larynx, thereby avoiding asphyxiation or pulmonary aspirations that could lead to the death of the patient.

It is suitable for use in operating theatres, emergency wards and out-patient hospitals, due to its efficacy, thanks to the internal visualisation offered by the said optical-light emitting laryngoscope. In the case of a traffic accident the individual involved may be attended to at the site, without having to be moved.

It may be used in any position, even with a single hand, without the need to force the cervical bones, and may be left on patients by using bands that pass behind the head.

It may be used with individuals who have a rigid neck brace fitted, or even those wearing crash helmets without protection for the jaw, or with removable jaw protection.

It may be used in places where there is little and restricted room, without losing any of its advantages in terms of safety, precision, speed and visualisation, for example in a vehicle where someone is trapped, due to its small size and the possibility of using it from any position respecting patients.

It may be kept in place following intubation, or be withdrawn after checking visually that the tube is correctly in place.

It may be re-inserted when an oral-tracheal tube has been left in place, to ensure that it is still correctly in position, or to change one oral-tracheal tube for another.

It may be used by non-medical health care staff, thanks to its ease of usage and safety.

Internal visualisation offers us the security of not only being sure of where to insert the oral-tracheal tube, but also awareness of the length of tube that has been inserted in the trachea, thanks to the indications on the body of the laryngoscope and thanks to the possibility of seeing the balloon of the oral-tracheal tube disappear through the tracheal glottis.

It may be used with patients who are only able to open their mouths to a limited amount, due to its small cross-section.

The time needed for intubation and the difficulty of this operation are not affected by the sex, height or obesity of patients, or by the "Mallampati" classification of the visibility of the airway at the larynx.

When this device is used neither the teeth nor the gums are harmed, as it is unnecessary to apply any force.

The characteristics of the device allow a range of materials to be used in manufacturing it, so that it can be made for very economical prices, using disposable and recyclable materials, depending on whether plastic or mechanical materials are used.

As well as the above-mentioned applications, the simplified optical-light emitting laryngoscope also makes it possible to:

Perform nasotracheal intubation, due to the vision it offers of the entire length of the nasotracheal tube, from the palate to the trachea.

Use the laryngoscope to find foreign bodies and extract them, using "Maguill" pincers.

DESCRIPTION OF THE FIGURES

To aid comprehension of this invention, which refers to an optical-light emitting laryngoscope, 20 figures are enclosed with this patent application with the aim of achieving better understanding of the fundamental aspects of the same, as well as better comprehension of the description of a preferential form of realisation of the invention, while taking into account the fact that these figures are illustrative in nature and are not restricting.

DESCRIPTION OF CERTAIN PREFERENTIAL EXAMPLES OF REALISATION

This invention may be better comprehended on the basis of the following detailed description, which shows the main characteristics of the optical-light emitting laryngoscope to which it refers.

Figure 3:
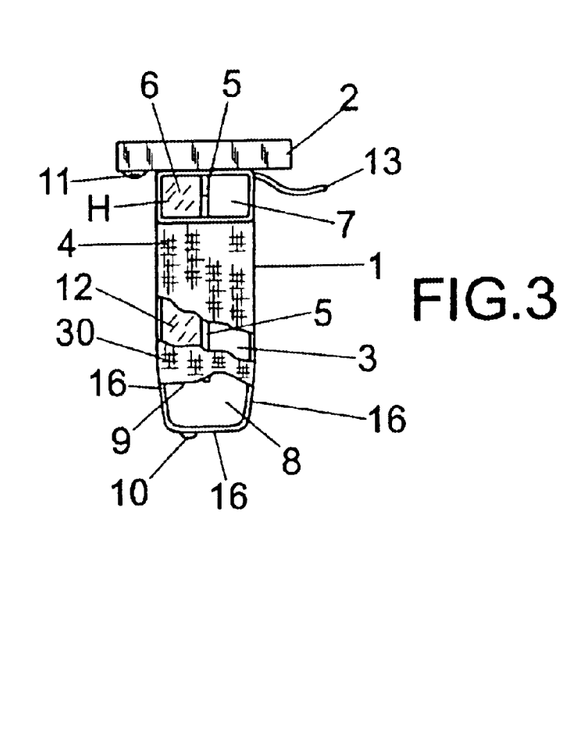
FIG. 3 shows the main profile of the optical-light emitting laryngoscope with an oral-tracheal guide, complementing the two previous figures.
Figure 4:
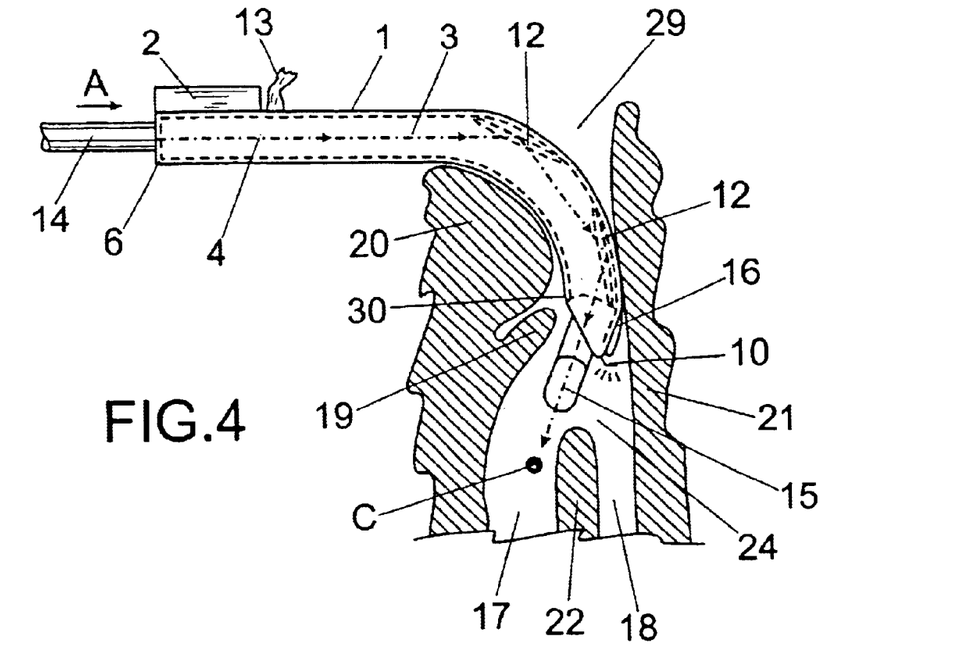
FIG. 4 shows the optical-light emitting laryngoscope with an oral-tracheal guide within the larynx of a patient during the insertion of the oral-tracheal tube, moving in direction A.

The particular configuration of the optical-light emitting laryngoscope with an oral-tracheal guide which is the subject of this invention is distinguished by the arrangement of its optical elements, a magnification lens 6 and surfaces to reflect the image 12, through the duct 4, in this case using economical elements such as mirrors, although it is also possible to use optic fibre suitable for this purpose in the same way. This said optic system makes it possible to inspect from the exterior, in the direction of vision shown by arrow B (FIGS. 2 and 3), how manoeuvres are progressing and the final moment when target point C is shown, this being necessary to gain access to the trachea 17, the duct of which 4 will be protected by a transparent shell 30 as a cover, all of this as shown in FIG. 4 and performed with a high degree of safety.

The arrangement of internal ducts 3 is distinguished, separated by the wall 5 of the optic duct 4, which makes it possible for the oral-tracheal tube 14 to pass through in the direction of insertion A, through the inlet 7 of the said duct 3, and which also allows air to circulate through the same.

All manipulation of the laryngoscope takes place outside the body of the patient, controlling the means of vision and illumination. At the right moment, when target point C is observed showing the opening of the trachea 17, the oral-tracheal tube 14 will be pushed, it being already in place in the duct 3, this pushing also being performed from the exterior.

Figure 5:
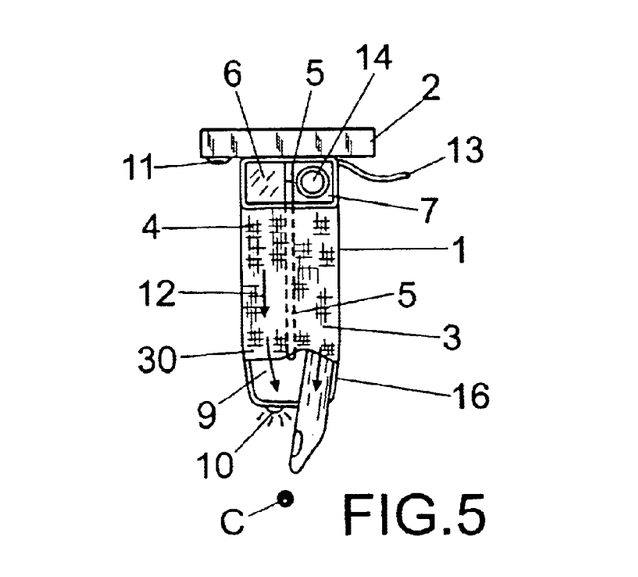
FIG. 5 coincides with FIG. 3, in the laryngoscope of which a tube has been inserted, the end of which can be seen protruding through the internal tip of the guide duct.

The shape of the outlets 8 and 9 of the body of the optical-light emitting laryngoscope with an oral-tracheal guide 1 is very important, with outlet guide walls 16. The outlets 8 and 9 of ducts 3 and 4 have walls 16 at the angles that are necessary to guide the end of the tube 15 over target point C, this orientation coinciding with the optical elements in use at each moment, surfaces to reflect the image or mirrors, or optic fibre. These walls 16 are moulded to the point of the oral-tracheal tube 14 in the shape of a spearhead (or chamfered) at its outlet 15 as is shown in FIG. 5, facilitating its sliding and making it possible to give the correct orientation to the oral-tracheal tube 14. The spearhead shape of the end of the oral-tracheal tube 15 is usual in all of the tubes used for intubation using known methods.

This arrangement of the walls 16, the inside of which makes it possible to align the elements for respiration also aid in the insertion of the laryngoscope into the mouth 25, pharynx 29 and larynx 24, adapting better to the patient's anatomy thanks to the resulting shape of its exterior surfaces.

The wall 5 functions by separating the two ducts 3 and 4, and is used to carry the wires connecting the light source 10 and a box of batteries 2 which supplies the necessary power, being activated by the switch 11 that is located on the same.

Figure 6:
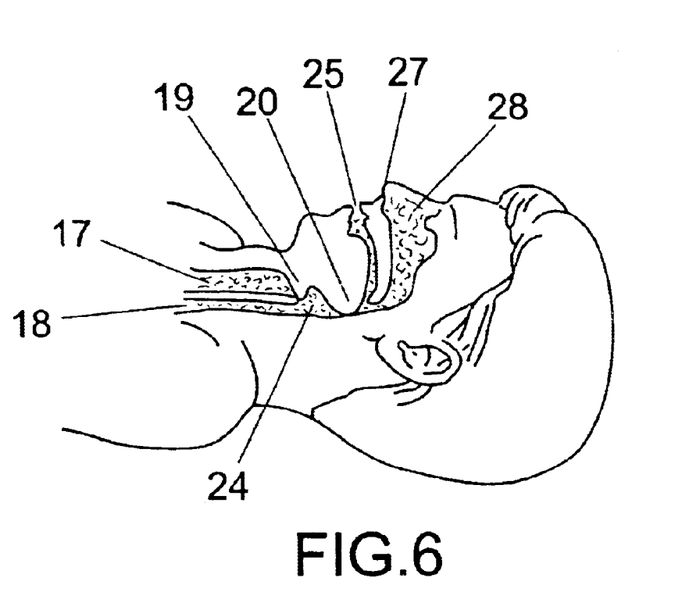
FIG. 6 shows upper part of an individual lying unconscious, with the resulting fall of the tongue and the epiglottis closing airway to the lungs.

The optical-light emitting laryngoscope with an oral-tracheal guide is of use, amongst other circumstances, when an individual is in an unconscious state (anaesthesia, surgery or multiple trauma), when as is shown in FIG. 6 their airway is blocked. In this case the larynx 24 is obstructed by the tongue 20 and the epiglottis 19 which fall into the rear part of the larynx 21, the duct of the trachea 17 being blocked at this moment and unable to receive air from the outside. It is of fundamental importance to unblock this airway, making involuntary or assisted respiration possible.

Figure 7:
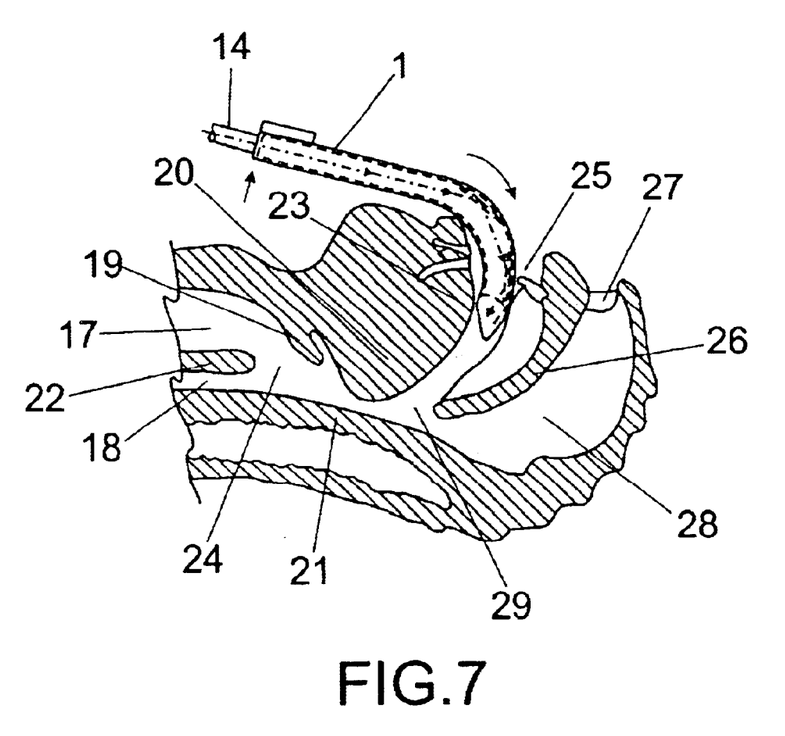
FIG. 7 shows diagram of a cross-section at the start of the operation of inserting the laryngoscope in the mouth of a patient.

In these cases when the optical-light emitting laryngoscope with an oral-tracheal guide 1 is used, it will be directly inserted by opening the patient's mouth 25 in the manner shown in FIG. 7, holding the tongue 20 with its curved part 23, this having an exterior anatomical shape which adapts to the same.

Figure 8:
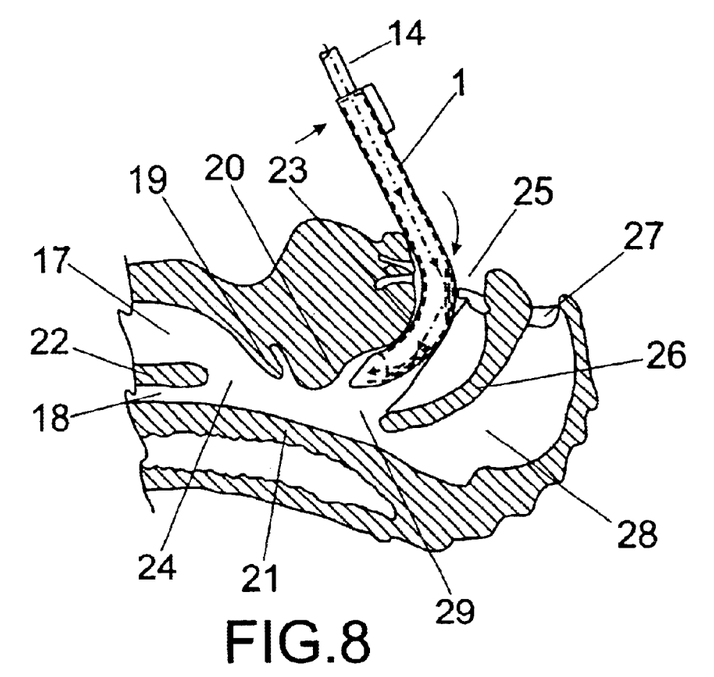
FIG. 8 shows a cross-section diagram in which it can be seen how the device, the optical-light emitting laryngoscope with an oral-tracheal guide, starts to hold the tongue due to its anatomical shape.
Figure 9:
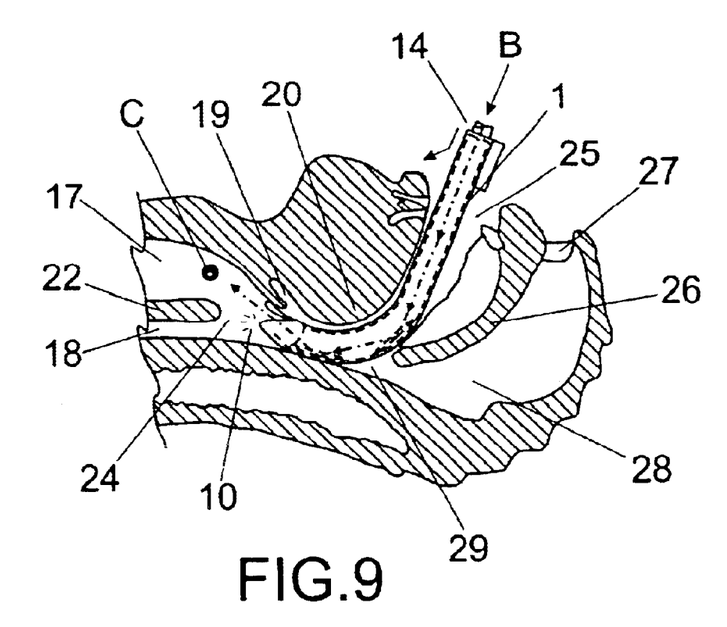
FIG. 9 shows a cross-section diagram of the end of insertion of the optical-light emitting laryngoscope with an oral-tracheal guide reaching the area of the larynx.
Figure 10:
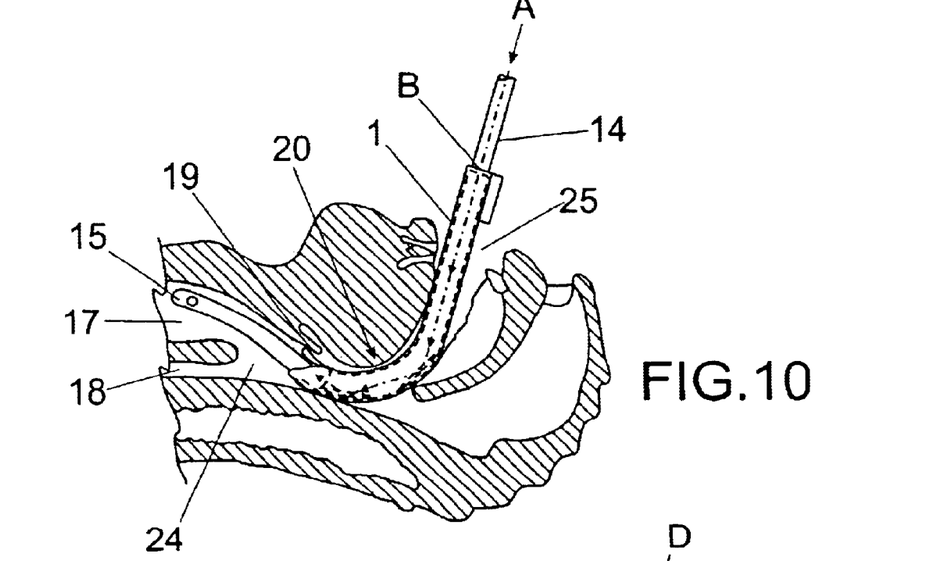
FIG. 10 shows a cross-section diagram of the end of the operation of intubation, with the end of the oral-tracheal tube already placed in the trachea.

Raising the tongue 20 at this moment and also raising the epiglottis 19, and opening the access to the trachea 17, according to what is shown in FIGS. 8 and 9, to be able to insert the oral-tracheal tube 14, 15 and intubate the patient, as seen in FIG. 10.

Figure 1:
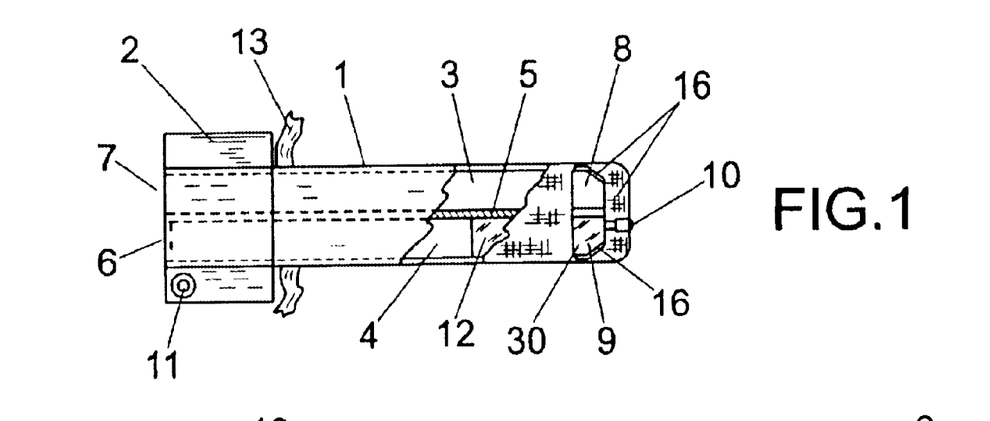
FIG. 1 shows a horizontal view of one of the main aspects of the optical-light emitting laryngoscope with an oral-tracheal guide that together with FIGS. 2 and 3 completes the overall view of the same.
Figure 2:
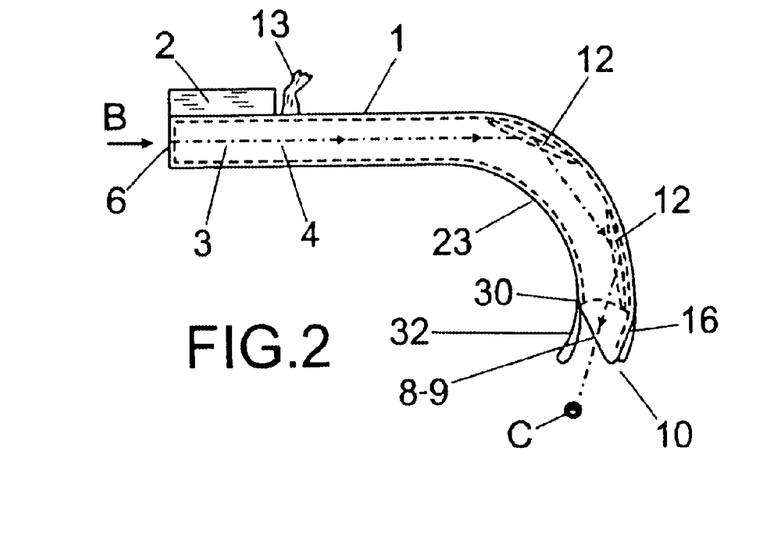
FIG. 2 shows the main vertical aspect of the optical-light emitting laryngoscope with an oral-tracheal guide, and complements FIGS. 1 and 3.

During these movements of the laryngoscope 1, from the start of the same as shown in FIG. 7, up to the end shown in FIG. 9, air is able to circulate through the laryngoscope through its duct 3 without any physical obstructions, the said movements being accompanied by continuous visual inspection, thanks to the optical system composed of a magnification lens 6, and the image reflecting elements 12, as well as the lighting system 10 and 2, in the body of the laryngoscope 1, as shown in FIGS. 1 and 2.

Optical illuminated inspection of the internal cavities of the mouth 25, pharynx 29 and larynx 24 in the direction of vision B, makes it possible to gain access to the zone in a way that is safer, faster and less traumatic, while always preventing the endotracheal tube from being inserted into the oesophagus 18 separated from the trachea 17 by the wall 22.

Once the optical-light emitting laryngoscope with an oral-tracheal guide has been placed in its definitive position, it is held on to the head of the patient by means of bands 13 (FIG. 5). It is possible to connect a manual or mechanical means of supplying oxygen to the adapter 39 which makes it possible using the said universal connection 38 to supply oxygen D through the tube 37.

Figure 11:
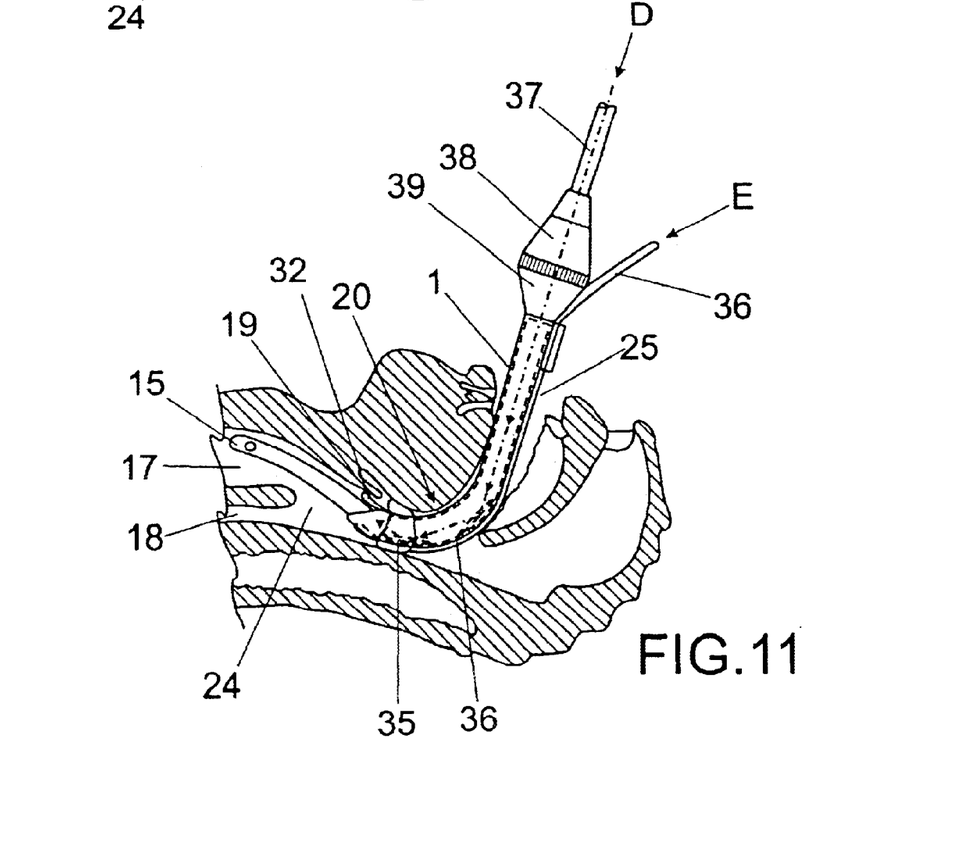
FIG. 11 shows a cross-section diagram of the complete ending of the operation of inserting the optical-light emitting laryngoscope with an oral-tracheal guide, in which it can be seen that an inflatable annular-shaped body is activated by means of introducing air into it through a tube connecting the said inflatable body to the outside, as well as an adapter for universal connection to any manual or mechanical means of introducing oxygen.
Figure 12:
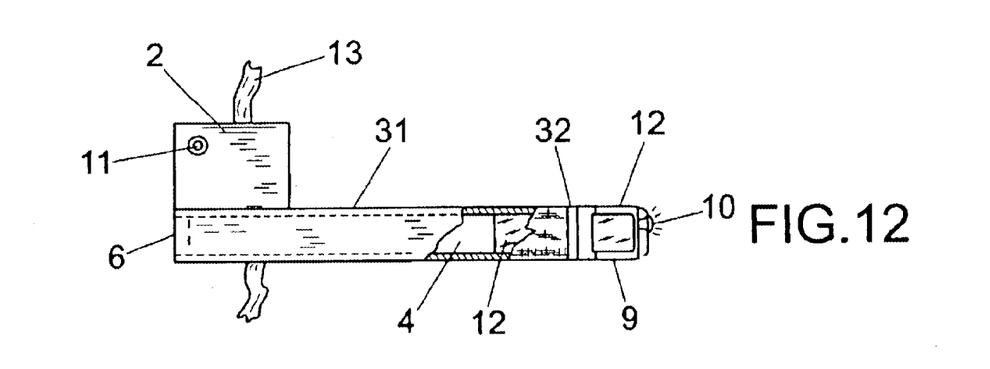
FIG. 12 shows a lower view than the vertical one shown in FIG. 3 of the simplified optical-light emitting laryngoscope of this invention.
Figure 13:
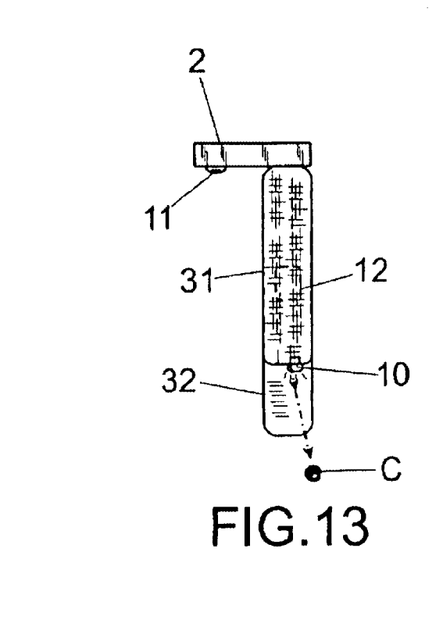
FIG. 13 shows the right hand profile of the simplified optical-light emitting laryngoscope.
Figure 14:
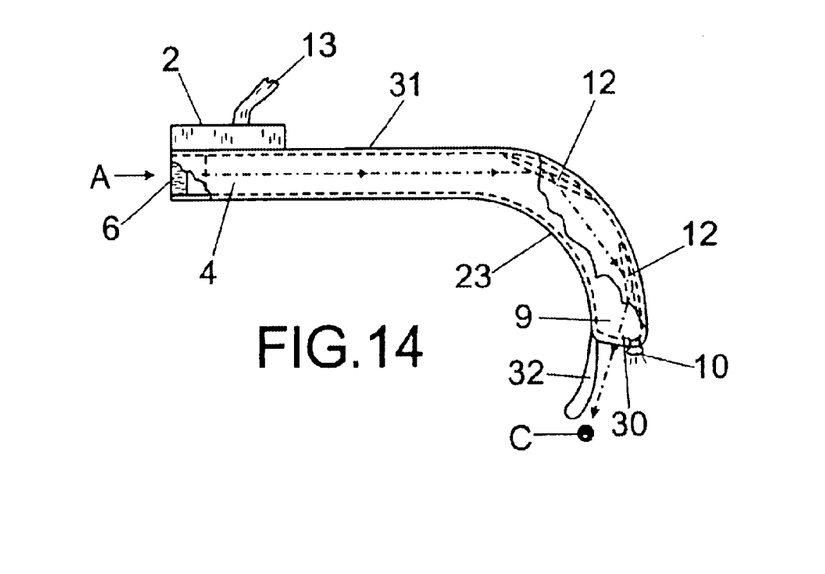
FIG. 14 shows the main vertical view of the simplified optical-light emitting laryngoscope.
Figure 15:
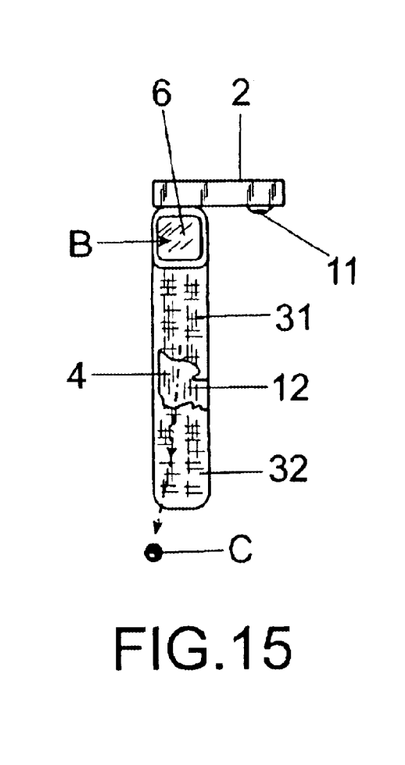
FIG. 15 shows the left—hand profile of the simplified optical-light emitting laryngoscope.
Figure 16:
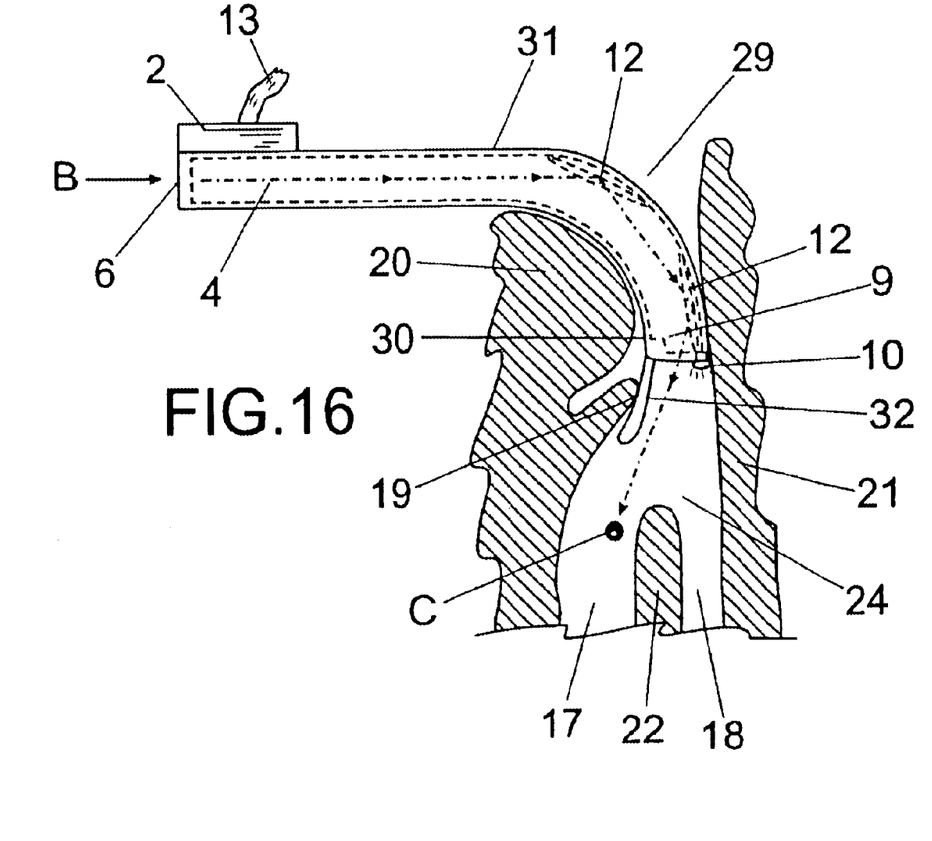
FIG. 16 shows the simplified optical-light emitting laryngoscope within the larynx.
Figure 17:
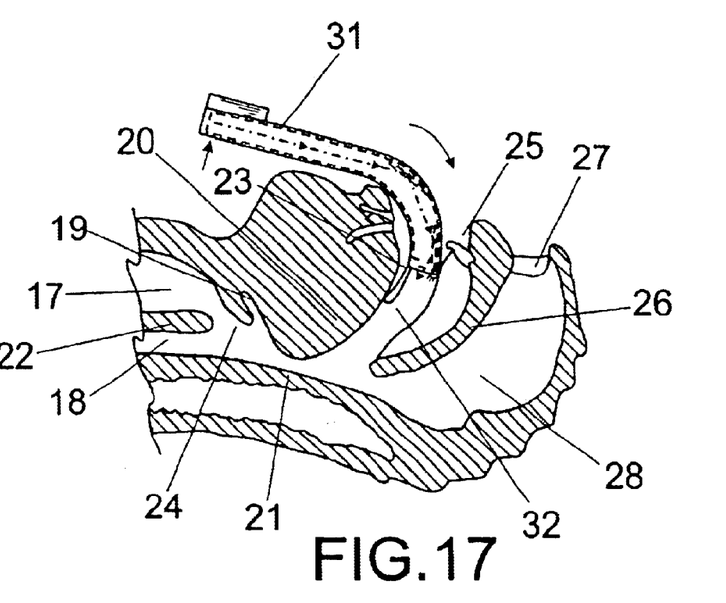
FIG. 17 shows a diagram illustrating the start of the operation of inserting the simplified optical-light emitting laryngoscope.
Figure 18:
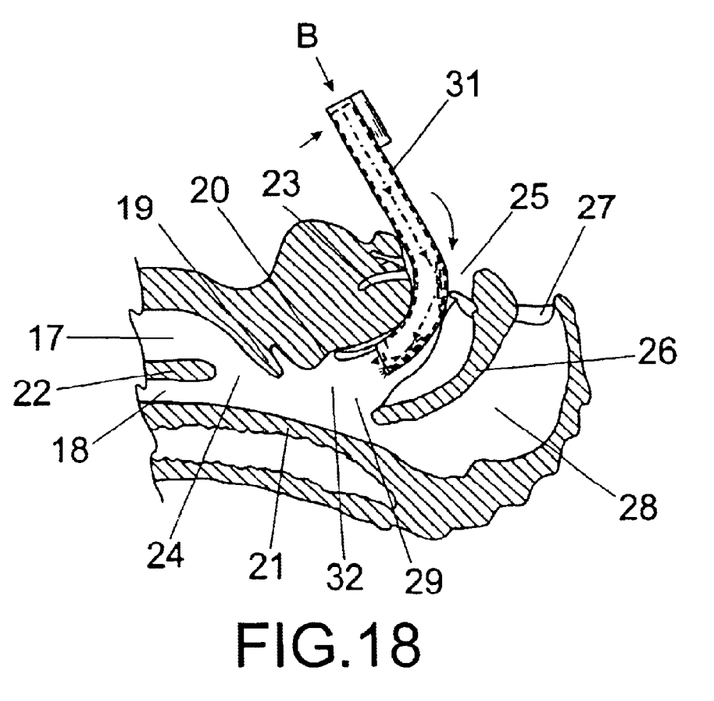
FIG. 18 shows the continuation of the insertion of the simplified optical-light emitting laryngoscope at the moment when it reaches the tongue, raising it.
Figure 19:
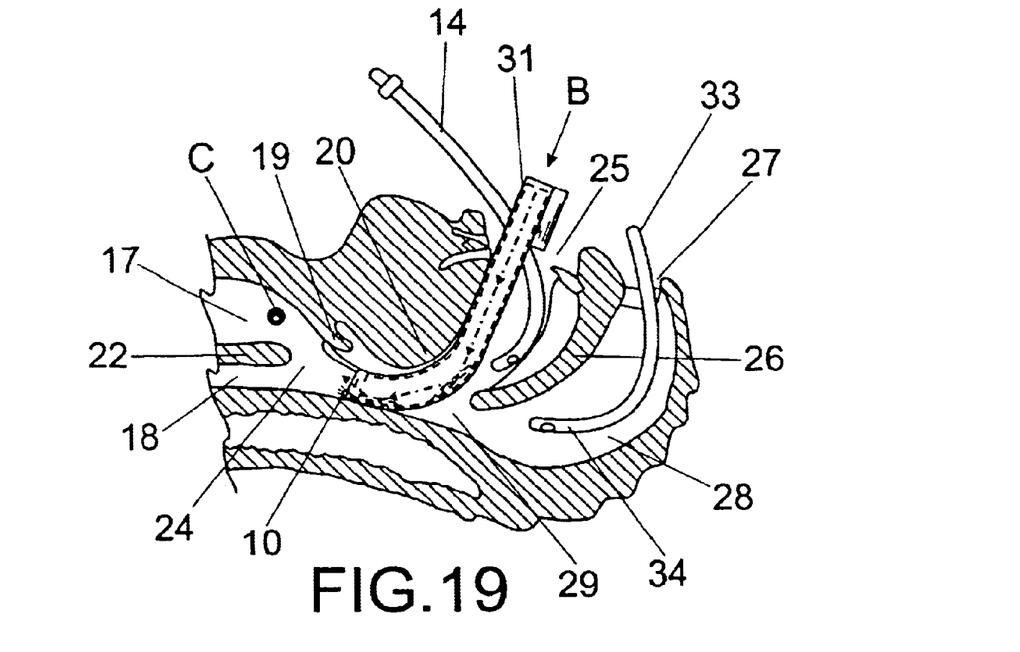
FIG. 19 shows the end of the operation of inserting the simplified optical-light emitting laryngoscope into the larynx, it being possible to see the possibility of inserting the endotracheal tube through the mouth or nose.
Figure 20:
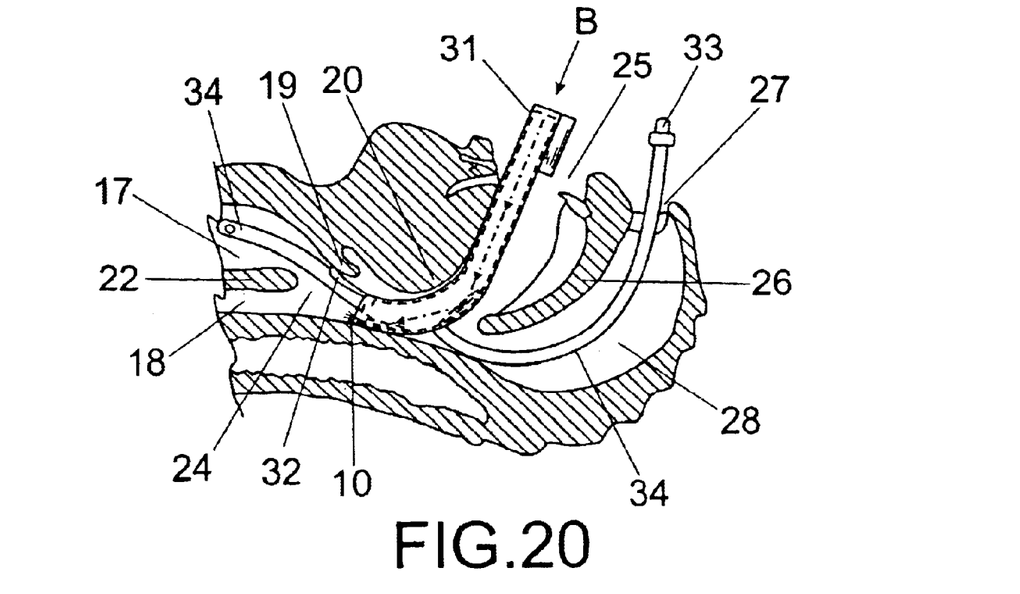
FIG. 20 shows the complete ending of the operation of intubation, in which the nasotracheal tube can be seen in place.

If added to the laryngoscope with an oral-tracheal guide 1, it is also possible to use an inflatable ring-shaped body 35 (FIG. 11), placed on the end of the laryngoscope 1 that is inserted into the patient. The said inflatable body 35 is useful for displacing the walls of the larynx and thereby improving the view of the same, as once the laryngoscope is in place air E is inserted through the inlet-outlet tube 36, inflating the annular body 35 and causing it to increase in diameter, exerting pressure against the internal walls of the larynx and fixing the laryngoscope 1 into the patient thanks to the bands 13.

Another characteristic of this laryngoscope 1 is that it is possible to fit a blade 32 at the end next to the curved section. This blade 32 may be fixed or mobile, and may be controlled from outside if the latter is the case. The purpose of this blade 32 is to facilitate the insertion of the laryngoscope 1 in the pharynx 29 and larynx 24 by raising the tongue 20 and the epiglottis 19, opening the airway and clearing the opening of the trachea 17 so that the oral-tracheal tube 14 can then be inserted.

It is possible to simplify the optical-light emitting laryngoscope with an oral-tracheal guide 1 and turn it into a simplified optical-light emitting laryngoscope 31, from which the oral-tracheal guide 3 has been eliminated, thereby reducing its size and thus making it possible to insert oral-tracheal tubes 14 as well as nasotracheal ones 33 and 34.

This simplified laryngoscope 31 has most of the elements described for the laryngoscope with an oral-tracheal guide 1, with the main difference that it has a single duct 4 containing optical elements 12 instead of the two ducts 3 and 4 of the laryngoscope described beforehand 1.

The arrangement of the several elements in the said laryngoscope 31 is similar to that of the previous one, with the optical elements, magnification lens 6 and image reflecting elements 12 located in the duct 4, and as is the case for the previous laryngoscope these reflecting elements are mirrors 12 due to economic reasons, the said mirrors 12 being angled at a previously set target point C and protected by a transparent shell 30 which functions as a cover. The image transmitted by the mirrors will always be real and not inverted, due to the existence of two mirrors, one after the other. This system may be replaced by one that uses optical fibre. This optical system makes it possible to inspect how operations are going from the outside whenever this is wished, as well as the final moment when target point C is visualised, this having been set to gain access to the trachea 17.

As was the case beforehand, the apparatus 31 is manipulated from outside the body of the patient. At the correct moment, once the laryngoscope 31 has been inserted and positioned at the target point C at the opening of the trachea 17, the oral-tracheal tube 14 will be inserted through the mouth 25, resting on the palate 26, or the nasotracheal tube 33 and 34 will be inserted through the nose 27, going through the nasal cavity 28, depending on the circumstances.

The laryngoscope 31 will visually maintain an angle of outlet towards target point C thanks to its optical system. The tube 14, 33 or 34 which is inserted will be positioned parallel to the body of the laryngoscope.

Both the optical-light emitting laryngoscope with an oral-tracheal guide 1 as well as the simplified version 31 are equipped with a blade 32 at the distal end of the body of the laryngoscope 3, which will hold and raise the epiglottis 19 from its under side, making it possible to obtain a clear view of the opening of the trachea 17 where target point C is located. The said blade may fixed, as in the figures, or mobile and controlled from the outside.

This simplified laryngoscope 31 is used in a similar way to the laryngoscope with an oral-tracheal guide 1, with the exception of the guide duct for inserting the endotracheal tube. The first steps involved in inserting the laryngoscope are the same as those described above, although once the laryngoscope has been positioned in its final location, i.e., with the tongue 20 and epiglottis 19 raised and therefore with the opening of the trachea 17 open, either an oral-tracheal tube 14 may be inserted through the mouth 25, or a nasotracheal tube 33 and 34 may be inserted through the nose 27.

Continuous visual inspection is possible during the insertion of the laryngoscope 31 as well as the endotracheal tube.

What is claimed is:

1. An optical-light emitting laryngoscope for naso-tracheal and/or oral-tracheal intubation and/or for visualizing the opening of the trachea, of the type comprising:
   a hollow, tubular main body having proximal end and a distal end such that proceeding from the proximal end is a first section that is straight and which continues to a second section that is anatomically curved in a shape for insertion into the inside of the mouth and the access zone of the larynx and terminating at the distal end which has angled walls; and
   a light source positioned at the distal end of the main body,
   wherein said main body provides an uninterrupted internal pathway for introduction of a device from the proximal end to the distal end thereof and wherein the main body includes a separate visualization duct positioned within the main body which extends from the proximal end to the distal end of the main body, the visualization duct comprising:
      an eyepiece lens located at the proximal end of the visualization duct; and
      a first and a second planar reflecting elements positioned in spaced apart relationship on an interior surface along the anatomically curved section of the visualization duct to enable viewing of reflected light and images through the proximal end during insertion of the laryngoscope and during insertion of any device into the trachea through the uninterrupted internal pathway.

2. An optical-light emitting laryngoscope according to claim 1, wherein the second planar reflecting element nearest the distal end of the main body is angled in relation with a longitudinal axis of the duct to permit direct observation of the opening of the trachea when the laryngoscope is in position for placement of the device into the trachea.

3. An optical-light emitting laryngoscope according to claim 2, wherein a transparent shell covers the distal end of the visualization duct.

4. An optical-light emitting laryngoscope according to claim 1, wherein a prism or a wide angled lens is positioned at the distal end of the visualization duct.

5. An optical-light emitting laryngoscope according to claims 1, wherein the uninterrupted pathway concludes at the distal end of the main body with guide walls formed of two centering side walls and a lower wall which raises the device to be inserted.

6. An optical-light emitting laryngoscope according to claim 1, wherein the light source is connected to a battery compartment located on the straight section of the main body adjacent the proximal end.

7. An optical-light emitting laryngoscope according to claim 1, wherein the main body further comprises means for holding the laryngoscope onto the body of the patient.

8. An optical-light emitting laryngoscope according to claim 7, wherein said holding means comprises bands that pass around the head, immobilizing the laryngoscope and device that has been inserted.

9. An optical-light emitting laryngoscope according to claim 1, wherein the distal end of the anatomically curved section includes an inflatable ring-shaped body which is activated by the introduction of air through a tube connecting the inflatable body to the outside.

10. An optical-light emitting laryngoscope according to claim 1, wherein the main body is equipped on the outside with visible graduations indicating the length of the main body that has been inserted into a patient.

11. An optical-light emitting laryngoscope according to claim 1, wherein at the proximal end of the uninterrupted pathway in the main body an adapter is provided for universal connection to a manual or mechanical means for introducing oxygen.

12. An optical-light emitting laryngoscope according to claim 1, wherein the main body is further equipped with articulated means for facilitating the insertion of the main body in the mouth for visualizing a target point.

13. An optical-light emitting laryngoscope according to claim 1, wherein a blade for raising the epiglottis is located at the distal end of the anatomically curved section of the main body.

14. An optical-light emitting laryngoscope according to claim 13, wherein the blade is mobile.

15. An optical-light emitting laryngoscope according to claim 1, wherein the planar reflecting elements are glass and/or plastic mirrors.

16. An optical-light emitting laryngoscope for naso-tracheal and/or oral-tracheal intubation and/or for visualizing the opening of the trachea, of the type comprising:
   a hollow, tubular main body having proximal end and a distal end such that proceeding from the proximal end is a first section that is straight and which continues to a second section that is anatomically curved in a shape for insertion into the inside of the mouth and the access zone of the larynx and terminating at the distal end which has angled walls; and
   a light source positioned at the distal end of the main body,
   wherein said main body provides an unblocked internal pathway forming an uninterrupted visualization duct from the proximal end to the distal end thereof, and wherein the visualization duct comprises:
      an eyepiece lens located at the proximal end of the visualization duct; and
      a first and a second planar reflecting elements positioned in spaced apart relationship on an interior surface along the anatomically curved section of the visualization duct to enable viewing of reflected light and images through the proximal end during insertion of the laryngoscope.

17. An optical-light emitting laryngoscope according to claim 16, wherein the second planar reflecting element nearest the distal end of the main body is angled in relation with a longitudinal axis of the duct to permit direct observation of the opening of the trachea when the laryngoscope is in position for placement of the device into the trachea.

18. An optical-light emitting laryngoscope according to claim 17, wherein a transparent shell covers the distal end of the visualization duct.

19. An optical-light emitting laryngoscope according to claim 16, wherein a prism or a wide angled lens is positioned at the distal end of the visualization duct.

20. An optical-light emitting laryngoscope according to claim 16, wherein the light source is connected to a battery compartment located on the straight section of the main body adjacent the proximal end.

21. An optical-light emitting laryngoscope according to claim 16, wherein the main body further comprises means for holding the laryngoscope on the body of the patient.

22. An optical-light emitting laryngoscope according to claim 21, wherein said holding means comprises bands that pass around the head, immobilizing the laryngoscope and device that has been inserted.

23. An optical-light emitting laryngoscope according to claim 16, wherein the distal end of the anatomically curved section includes an inflatable ring-shaped body which is activated by the introduction of air through a tube connecting the inflatable body to the outside.

24. An optical-light emitting laryngoscope according to claim 16, wherein the main body is equipped on the outside with visible graduations indicating the length of the main body that has been inserted into a patient.

25. An optical-light emitting laryngoscope according to claim 16, wherein the main body is further equipped with articulated means for facilitating the insertion of the main body in the mouth for visualizing a target point.

26. An optical-light emitting laryngoscope according to claim 16, wherein a blade for raising the epiglottis is located at the distal end of the anatomically curved section of the main body.

27. An optical-light emitting laryngoscope according to claim 26, wherein the blade is mobile.

28. An optical-light emitting laryngoscope according to claim 16, wherein the planar reflecting elements are glass and/or plastic mirrors.

29. An optical-light emitting laryngoscope according to claim 1, wherein the planar reflecting elements are placed adjacent each other in the longitudinal direction and on the same side of the visualization duct.

30. An optical-light emitting laryngoscope according to claim 16, wherein the planar reflecting elements are placed adjacent each other in the longitudinal direction and on the same side of the visualization duct.

* * * * *